US 12,064,137 B2

United States Patent
Erkamp et al.

(10) Patent No.: US 12,064,137 B2
(45) Date of Patent: Aug. 20, 2024

(54) NEEDLE WITH MULTIPLE SENSORS

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Francois Guy Gerard Marie Vignon, Croton On Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 15/301,611

(22) PCT Filed: Apr. 1, 2015

(86) PCT No.: PCT/IB2015/052381
§ 371 (c)(1),
(2) Date: Oct. 3, 2016

(87) PCT Pub. No.: WO2015/155632
PCT Pub. Date: Oct. 15, 2015

(65) Prior Publication Data
US 2017/0020562 A1   Jan. 26, 2017

Related U.S. Application Data

(60) Provisional application No. 61/978,222, filed on Apr. 11, 2014.

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/4494* (2013.01);
(Continued)

(58) Field of Classification Search
CPC ........... A61M 25/0108; A61B 17/3403; A61B 2034/2063; A61B 8/0841; A61B 8/4494;
(Continued)

(56) References Cited

U.S. PATENT DOCUMENTS 4,697,595 A   10/1987   Breyer
4,706,681 A   11/1987   Breyer
(Continued)

FOREIGN PATENT DOCUMENTS

CA   1326192 C   *   1/1994   .......... A61B 8/0833
JP   2013027513 A       2/2013
(Continued)

OTHER PUBLICATIONS

Wendeberg et al.; Anchor-free TDOA self-localization; published in Sep. 2011; 2011 International Conference on Indoor Positioning and Indoor Navigation; Guimaraes, Portugal, 2011, pp. 1-10, doi: 10.1109/IPIN.2011.6071909. (Year: 2011).*
(Continued)

*Primary Examiner* — Chao Sheng

(57) ABSTRACT

A medical device includes an elongated body (14) and a plurality of sensors (10) conformally formed on the elongated body at a plurality of longitudinal positions along the elongated body. The plurality of sensors is configured to generate signals in accordance with detected energy for an imaging system. A single electrical trace (24) connects to each of the plurality of sensors, the plurality of sensors being connected in parallel to form an array of sensors along the elongated body.

23 Claims, 3 Drawing Sheets

(51) Int. Cl.
  *A61B 8/08* (2006.01)
  *A61B 34/20* (2016.01)
  *A61M 25/01* (2006.01)
  *A61B 90/00* (2016.01)

(52) U.S. Cl.
  CPC ......... *A61B 34/20* (2016.02); *A61M 25/0108* (2013.01); *A61B 2017/3413* (2013.01); *A61B 2034/2063* (2016.02); *A61B 2090/3929* (2016.02)

(58) Field of Classification Search
  CPC ................ A61B 17/3413; A61B 34/20; A61B 2090/3929
  See application file for complete search history.

(56) References Cited

U.S. PATENT DOCUMENTS

| | | | | |
|---|---|---|---|---|
| 5,672,172 | A * | 9/1997 | Zupkas | A61B 8/12 606/20 |
| 6,206,831 | B1 * | 3/2001 | Suorsa | A61B 18/1492 600/439 |
| 6,216,027 | B1 * | 4/2001 | Willis | A61B 5/0422 600/424 |
| 6,217,518 | B1 * | 4/2001 | Holdaway | A61B 5/6848 600/439 |
| 6,305,225 | B1 * | 10/2001 | Bae | G01S 7/52046 600/447 |
| 2002/0060508 | A1 * | 5/2002 | Sudol | B06B 1/0629 310/334 |
| 2003/0060700 | A1 | 3/2003 | Solf | |
| 2006/0235314 | A1 | 10/2006 | Migliuolo | |
| 2007/0239017 | A1 * | 10/2007 | Knowles | A61B 8/12 600/459 |
| 2007/0276232 | A1 * | 11/2007 | Towe | A61B 8/0833 600/437 |
| 2008/0089181 | A1 * | 4/2008 | Adachi | B06B 1/0292 367/189 |
| 2009/0058228 | A1 * | 3/2009 | Wakabayashi | B06B 1/0292 310/334 |
| 2011/0166455 | A1 | 7/2011 | Cully | |
| 2014/0092710 | A1 * | 4/2014 | Farhadiroushan | G01S 5/20 367/117 |

FOREIGN PATENT DOCUMENTS

| | | |
|---|---|---|
| RU | 2328318 C1 | 7/2008 |
| RU | 2332168 C1 | 8/2008 |
| WO | 199839668 A1 | 9/1998 |
| WO | 2012172458 A1 | 12/2012 |
| WO | 2015155645 A1 | 10/2015 |

OTHER PUBLICATIONS

Barr, Richard G. "Improved Needle Visualization with Electronic Beam Steering", Ultrasound Quarterly, vol. 28, No. 2, Jun. 2012.

Nichols, Kremer et al "Changes in Ultrasonographic Echogenicity and Visibility of Needles with Changes in Angles of Insonation", J Vasc Interv Radiology, vol. 14, No. 12, 2003.

Cheung, Stphanic et al "Enhancement of needle visibility in ultrasound-guided percutaneous procedures", Ultrasound in Medicine & Biology, vol. 30, Issue 5, May 2004—Abstract Only.

* cited by examiner

NEEDLE WITH MULTIPLE SENSORS

CROSS-REFERENCE TO PRIOR APPLICATIONS

This application is the U.S. National Phase application under 35 U.S.C. § 371 of International Application No. PCT/IB2015/052381, filed on Apr. 1, 2015, which claims the benefit of U.S. Provisional Patent Application No. 61/978,222, filed on Apr. 11, 2014. These applications are hereby incorporated by reference herein.

BACKGROUND

Technical Field

This disclosure relates to medical instruments and more particularly to a system and method to track a tip of a device under ultrasound guidance using multiple ultrasound sensors connected in parallel using a same interconnect (trace).

Description of the Related Art

In ultrasound imaging, the visibility of the needle is often very poor due to the specular nature of the needle surface that reflects beams away from the imaging probe. To alleviate this problem some needle manufacturers have produced needles with special echogenic coatings, but the visualization improvement is limited. Ultrasound imaging system manufacturers have developed algorithms that use multiple imaging beams from varied angles, but improvement is limited and such a strategy is primarily suited only for linear arrays. Both strategies do not help when the needle is inserted perpendicular to the imaging plane or the needle path has a small offset relative to the imaging plane.

One solution that has been proposed to visualize the tip of interventional tools such as needles, but also catheters, is to add ultrasound receivers near the tip of the tool. While the imaging beam sweeps the field of view, the signals from the sensors indicate how close the beams are getting to the sensor. This information is used to calculate sensor position relative to the ultrasound image with positional accuracy exceeding 0.5 mm, even under conditions where the needle is not visible in the ultrasound image. The sensor needs to not interfere with the functionality of the device (e.g., an automatic biopsy device), that is, not block the lumen, not interfere with the mechanics, etc.

SUMMARY

In accordance with the present principles, a medical device includes an elongated body and a plurality of sensors conformally formed on the elongated body at a plurality of longitudinal positions along the elongated body. The plurality of sensors is configured to generate signals in accordance with detected energy for an imaging system. A single electrical trace connects to each of the plurality of sensors, the plurality of sensors being connected in parallel to form an array of sensors along the elongated body.

Another medical device includes an elongated body and three or more sensors conformally formed on the elongated body at a plurality of longitudinal positions along the elongated body. The three or more sensors are spaced apart from adjacent sensors by a gap. Each gap has a distance configured to assist in computing which sensor received a measured signal. The three or more sensors are configured to generate signals in accordance with detected energy for an imaging system. An electrical trace connects to the three or more sensors. The three or more sensors are connected in parallel to form an array of sensors along the elongated body.

A method for determining deciphering received signals in a medical device includes providing a medical device having an elongated body, a plurality of sensors conformally formed on the elongated body at a plurality of longitudinal positions along the elongated body, an electrical trace connecting to the plurality of sensors, the plurality of sensors being connected in parallel to form an array of sensors along the elongated body; generating signals at a position by an imaging system; receiving the signals by the plurality of sensors; and separating the signals received by the plurality of sensors by employing variable spacings between and geometric positions of the plurality of sensors to determine which sensor received which signals.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1A:
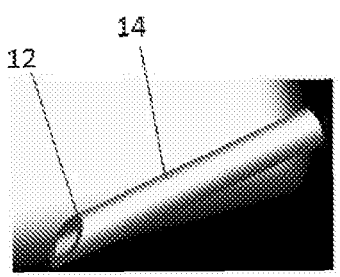
FIG. 1A is a perspective view showing a needle where a plurality of sensors will be formed in accordance with the present principles.

In accordance with the present principles, systems, devices and methods are provided for tracking a needle (or other device) under ultrasound guidance by attaching small ultrasound receivers onto the device. The present principles provide a needle, device or system that includes two or more low profile sensors at very low per device cost and permits scaling for mass production to maintain low cost.

Bringing out all the signals from individual sensors on the needle creates a more complex interconnect between sensors along the needle and connecting structures on a hub end portion (proximal end portion). This is especially true if low cost piezoelectric materials are employed, as each sensor needs its own stripline-like interconnect to avoid severe crosstalk between sensors.

To avoid this complexity and reduce fabrication cost of the needle, sensors are connected together (in parallel) using a single shared signal trace. A strong signal will be observed when the imaging beam hits one of the sensors. Thus, when the needle is roughly in the imaging plane, strong signals should be observed over the course of an imaging frame. Knowledge of the beam scanning order permits a determination of what strong signal was received by what sensor.

In particularly useful embodiments, a single signal trace is shared by multiple sensors along the needle or other device. Knowledge of the beam scanning pattern is employed to separate out the individual sensor signals.

The ultrasound sensors may be formed on the needle or other device and may be fabricated using a piezoelectric polymer, e.g., polyvinylidene fluoride (PVDF) or polyvinylidene fluoride trifluoroethylene (P(VDF-TrFE)). P(VDF-TrFE), which can be dissolved in acetone and applied to the needle through an evaporative process. The sensors are high impedance and can be modeled individually as a voltage source in series with a small capacitor (e.g., 2.2 pF). Such a sensor is very sensitive to capacitive loading of the electrical interconnect, and special capacitance cancelling electronics (similar to, e.g., a driven shield technique) can be employed to avoid large signal loss. A wire carrying the signal preferably is shielded (e.g., includes an electric shield around the conductor). This may be accomplished using a stripline configuration.

It should be understood that the present invention will be described in terms of medical instruments; however, the teachings of the present invention are much broader and are applicable to any instrument that can accept multiple low profile sensors. In some embodiments, the present principles are employed in tracking or analyzing complex biological or mechanical systems. In particular, the present principles are applicable to internal tracking procedures of biological systems and are applicable for procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1B:
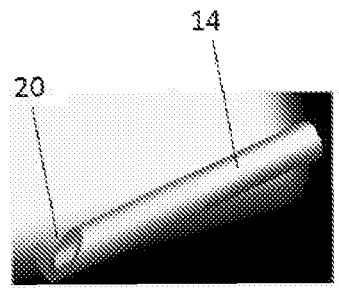
FIG. 1B is a perspective view showing the needle of FIG. 1A having a copolymer (piezoelectric polymer) formed thereon in accordance with the present principles.
Figure 1C:
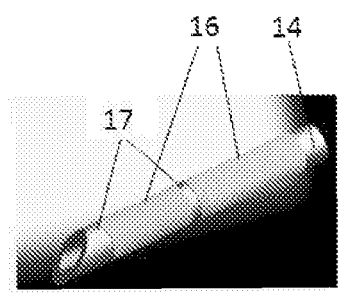
FIG. 1C is a perspective view showing the needle of FIG. 1B having a dielectric layer (insulator) formed thereon in accordance with the present principles.
Figure 1D:
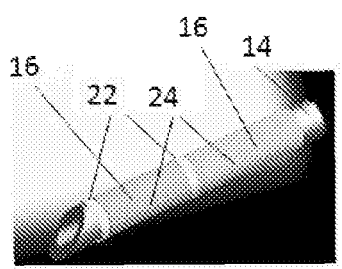
FIG. 1D is a perspective view showing the needle of FIG. 1C having top electrodes formed on the copolymer and a single trace formed on the dielectric layer in accordance with the present principles.
Figure 1E:
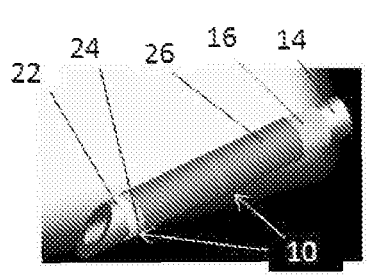
FIG. 1E is a perspective view showing the needle of FIG. 1D having another dielectric layer (insulator) formed on the trace in accordance with the present principles.

Referring now to the drawings in which like numerals represent the same or similar elements and initially to FIGS. 1A-1F, perspective views showing the fabricating of multiple ring sensors 10 on a tip 12 of a needle 14 are illustratively shown in accordance with one embodiment. On the bare needle 14 (FIG. 1A), a copolymer (piezoelectric) layer 20 is deposited (FIG. 1B) over a region where the sensors 10 are to be formed. A dielectric layer 16 is applied (FIG. 1C) with gaps, sections or spaces 17 left open where the sensors 10 are to be formed. Top electrodes 22 and a connecting trace 24 for the sensors 10 are formed (FIG. 1D). In FIG. 1E, another dielectric layer 26 is formed, and a conductive outer shield 28 is applied in FIG. 1F.

Referring to FIG. 1A, the needle 14 is depicted prior to the formation of sensors 10. The needle 14 preferably includes a metal, such as a stainless steel although other surgically compatible materials may be employed.

Referring to FIG. 1B, the tip portion (distal end portion) of the needle 14 is coated with the piezoelectric copolymer 20. This may be achieved by employing a dip coating process or an additive material process (e.g., evaporation or other deposition method). The metal needle 14 now serves as a bottom electrode for the copolymer sensors 10. In one embodiment, the copolymer includes a P(VDF-TrFE) material, although other suitable materials may be employed.

Referring to FIG. 1C, the dielectric layer or insulator 16 is deposited or printed on the needle 14. The insulator 16 may include any suitable dielectric material that adheres to the needle 14. The insulator 16 may be about 25-50 microns thick although other thicknesses may be employed. The insulator 16 is deposited on the needle 14 without covering sections 17, preferably near the tip region and a predetermined proximal distance from the tip region. This may be accomplished in a plurality of ways. For example, the portion may be masked and material in section 17 may be etched away.

Referring to FIG. 1D, the top electrode 22 and the signal trace 24 connecting to the top electrodes 22 are applied. The top electrodes 22 are formed over the copolymer 20 at the distal end portion, and the trace 24 is formed over a portion of the insulator 16. The top electrodes 22 are connected together by the trace 24. The top electrodes 22 are therefore connected in a parallel configuration. The trace 24 may continue proximally along the needle 14 (on the insulator 16) and connect to a hub contact or pad (not shown), which may also be formed using the same processing as the top electrode 22 and trace 24. The top electrodes 22, hub contact and the trace 24 may be printed using a conductive ink. Other processes may be employed as well such as, e.g., masked vapor deposition or vapor deposition and etching. The material for top electrode 22, hub contact and trace 24 may also include deposited metals such as silver, gold, etc. The top electrode 22, hub contact and the trace 24 may have a thickness of less than one micron to a few microns.

Referring to FIG. 1E, another insulator 26 is formed over the trace 24 and insulator layer 16. This insulator 26 may be produced by dip coating from the proximal end on the needle 14. The insulator 26 is deposited or printed on the needle 14. The insulator 26 may include any suitable dielectric material that adheres to underlying materials. The insulator 26 may be about 25-50 microns thick although other thicknesses may be employed. The insulator 26 is not formed over the distal-most top electrode 22.

Figure 1F:
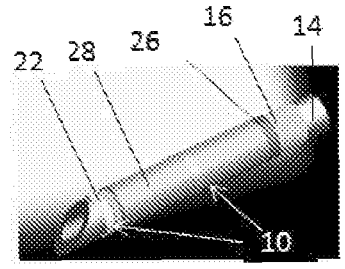
FIG. 1F is a perspective view showing the needle of FIG. 1E having a conductive shield formed thereon in accordance with the present principles.

Referring to FIG. 1F, the conductive shield 28 is applied over the insulator 26. The conductive shield 28 may be produced by vapor deposition or dip coating in conductive ink. Care needs to be taken to not cover the tip (distal end portion of the needle 14). The needle 14 and outer shield 28 will be coupled together as they form a driven shield. To electrically insulate the top electrode 22 from the surroundings and ensure biocompatibility, the whole needle could be covered with, for example, parylene or other outer dielectric material (not shown). If the parylene coating (outer dielectric) is extremely thin, there may be a capacitive coupling from the top electrode 22 to a body (where the needle 14 will be inserted) and the body to the outer shield 28. With a conductive body, this could create a shunt path across the sensors 10 and thus form a low pass filter. Care needs to be taken that the cut off frequency is significantly above the ultrasound frequency of interest. Alternatively, the dielectric 26 and outer shield 28 could be made to go over the tip, thereby insulating the distal-most top electrode 22 (but possibly slightly degrade sensitivity as the acoustic wave has to pass through it). By properly selecting acoustic properties and thickness the outer dielectric (and/or insulator 26) may serve as an acoustic matching layer.

For the dielectric layers, e.g., insulators 16, 26 and the outer dielectric, it is advantageous to select a material with a relatively low dielectric constant. For example, polytetrafluoroethylene (PTFE) with a dielectric constant of about 2.1 may be selected. However, the adhesion of PTFE to other materials may be an issue. Other materials, such as biocompatible polypropylene (dielectric constant 2.2) may be employed. Many plastics/polymers have a dielectric constant close to 3.0 and may also be employed. Polyurethane has a slightly higher 3.5 value and is attractive for use in the present applications because there are medical grade versions (used to coat implantable pacemakers). Further, polyurethane provides good adhesion to many materials with high smoothness and durability, and can be deposited in thin layers using appropriate solvents. Other materials may also be used.

Sensors 10 provide maximum sensor sensitivity due to a strong impedance difference between the sensor 10 and its backing material (e.g., piezoelectric material). The narrow trace 24 is provided that minimizes the capacitive loading of the sensors 10. The thin interconnect trace 24 is shielded similarly to a stripline configuration to be optimized for low capacitance. The sensors 10 can be more sensitive to injected noise as the needle 14, that is in electrical contact with tissue (when filled with fluid or stylet), is part of the interconnect.

The sensors 10 may include a P(VDF-TrFE) copolymer ring 20 shaped onto the needle 14. A hub contact or pad (not shown, see FIG. 2) is connected of the top electrode 22 and is formed at a hub end portion (proximal end portion) and provides for low disposable cost connectivity. Specialized electronics can be provided to reduce signal loss due to capacitive loading of the interconnect.

Multiple sensors 10 are provided on a same needle 14 and share a common trace 24. Although two sensors 10 are depicted, more than two sensors 10 may be formed along the needle 14 or other device. This permits a determination of orientation of the needle and also a determination of the location of the needle tip without the need to place the sensor very close to the tip. Calculating the tip location based on signals from multiple sensors 10 should also increase the measurement accuracy as well as provide an indication of confidence in the measurement. The cost is a slightly more complicated manufacturing process and a slight loss of signal because of the extra capacitive load of multiple sensors.

When the needle 14 is slowly inserted into an imaging plane of an ultrasound transducer (transmitter) or probe, at first only the sensor 10 at the tip of the needle 14 (distal-most sensor 10) will be in the imaging plane, and a single large signal is received by the distal-most sensor 10 for every imaging frame. This signal is associated with the ring sensor 10 at the tip (e.g., distal most sensor 10). Now, as the needle 14 is pushed in deeper, a temporal shift of that signal can be tracked and the association between that signal and the tip sensor 10 can be maintained. When a second sensor 10 enters the imaging plane and a second signal starts appearing, this signal is from the sensor 10 closer to the hub end (proximal end). This signal can now also be tracked from frame to frame to maintain the association between that peak and the hub side sensor.

Alternatively, some physical characteristics or assumptions could be employed to separate out the signals. In most applications, the needle 14 will be inserted relatively close to a footprint of the transducer, and its orientation will have a component along the imaging beam direction. When two signals are received over the course of a frame, it can be assumed that the tip sensor signal is further away from the probe (transducer) than the hub side sensor signal. Thus, the signal that has the longer delay with respect to a line trigger, is the signal that belongs to the tip sensor 10.

Figure 2:
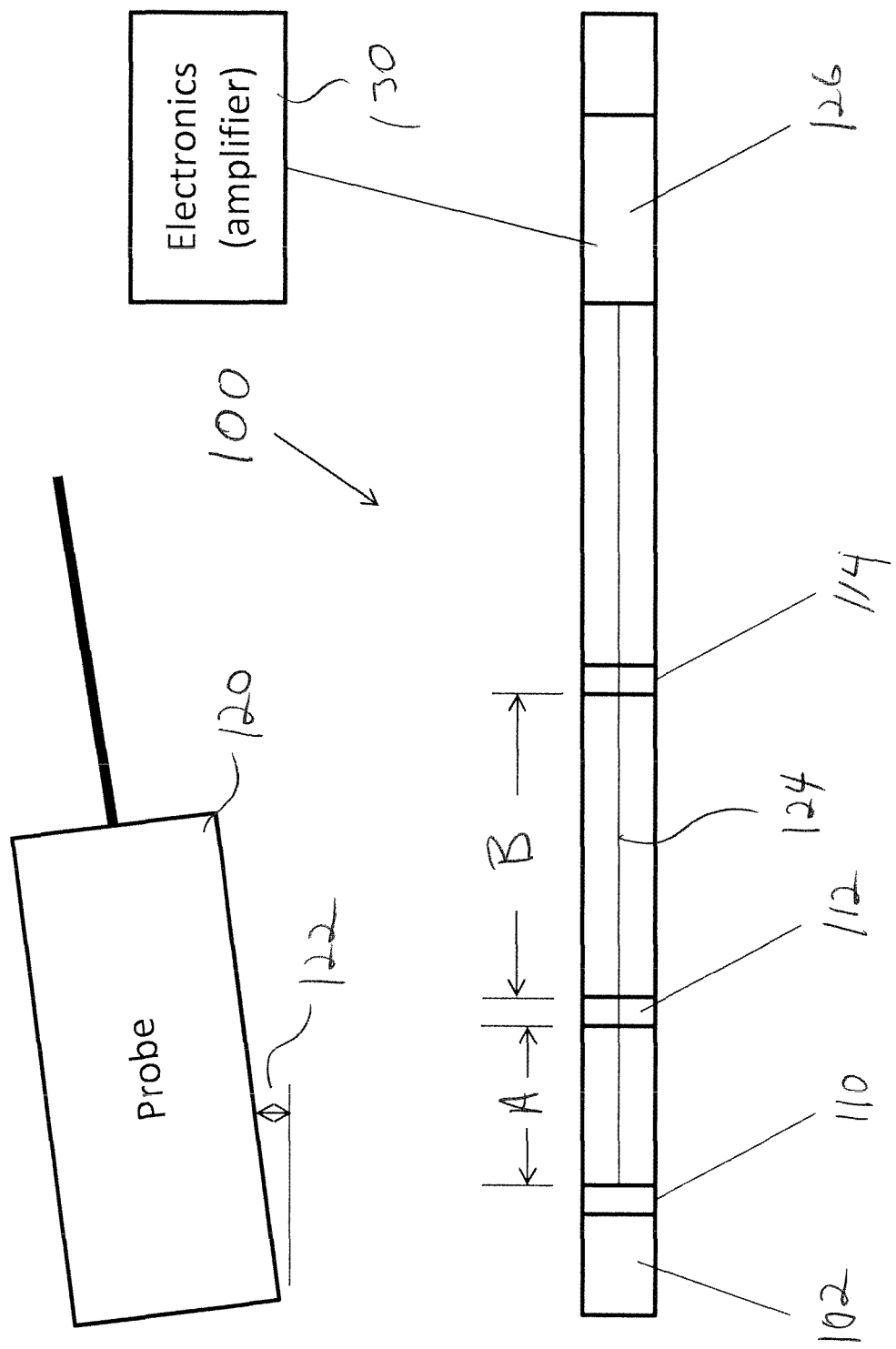
FIG. 2 is a side schematic view showing a needle where three or more sensors are formed in accordance with the present principles.

Referring to FIG. 2, a schematic side view of a needle 102 having a plurality of sensors 110, 112, 114 connected by a single trace 124 is shown in accordance with one embodiment. Although three sensors 110, 112, 114 are shown, a larger number of sensors can be connected to the single trace 124. The same methods as described above can be employed to separate out the signals.

In addition, there are other mechanisms that may be employed to separate the signals. For example, if the sensors are spaced apart according to specific distances or ratios, the variable spacing can be exploited to separate the signals. In a three sensor needle arrangement 100, where a space between a tip sensor 110 and middle sensor 112 is A (e.g., 5 mm) and between the middle sensor 112 and a hub side sensor 114 is B (e.g., 10 mm). A delay between a line trigger signal (for the ultrasound imaging system) and a signal from each strong signal may be considered. This delay is proportional to the distance between the sensor 110, 112 or 114 and a probe 120. The difference in this delay for a linear array is proportional to both the spacing A or B between the sensors 110, 112, 114 and an angle 122 of the needle 114 relative to the probe 120. Assuming a stiff needle, the angle is the same for all sensors 110, 112, 114. Thus, the difference in delay between sensor 110 and 112 is going to be half of the difference in delay between sensor 112 and 114 (if evenly spaced, for example), and this information can be used for signal separation.

A hub contact 126 is formed on a proximal end portion of the needle 102 (or other elongated device). The trace 124 connects to the hub contact 126 and the hub contact 126 connects to electronic circuits 130, e.g., an amplifier or other receiver circuits. The electronic circuits 130 may also connect to a shield (not shown) over the trace 124 and the needle 102 using a connector or connectors. The electrical connections may change depending on the circuits and the needle arrangement employed.

In the case of many (>3) sensors, the time difference between all possible combinations of sensors can be used to separate out the signals. A multitude of alternative embodiments will be readily apparent to one of ordinary skill in the art, without departing from the essential elements of this disclosure. For example, the sensors do not have to be directly deposited onto the needle surface. In one example, an insulator and metallization layer forming the inner shield may be formed upon which sensors are deposited (on top) so they are insulated from the needle shaft. In another example, an insulating layer can be deposited on the needle, then a shared signal trace and bottom electrodes are formed on the insulator, followed by piezoelectric material for the sensors. An outer conductive shield that also forms the top electrode for all sensors may be provided.

In one embodiment, more than one shared trace may be employed on a needle, for example, sensors one, three, five share one trace, and sensors two, four, six share another trace. This can increase the distances between sensors within a set and make signal separation more robust. The sensors do not have to be made with PVDF or copolymer. The sensors could, for example, include PZT or another piezoelectric material, or be an altogether different type of sensor, for example, capacitive micromachined ultrasound transducers. (CMUT).

If additive manufacturing techniques such as conformal micro dispensing techniques, spray paint or inkjet printing are employed, it may be advantageous to deposit the materials for the interconnect stripline (traces) over a smaller section of the circumference. For example, if the dielectric is applied using a spray paint or airbrush technique, a wide spray pattern could deposit on multiple needles simultaneously and would naturally create a tapered coating spanning 180 degrees of the circumference. Alternatively a narrow spray pattern with an airbrush could produce a tapered dielectric layer over a much smaller circumferential area, for example 45 degrees. In other words, the ring structure would not encircle the entire needle or device and instead occupy a section on the circumference.

In one embodiment, e.g., FIGS. 1A-1F, a first dielectric spanning 45 degrees could be applied, then a narrow trace with, for example, a micro dispensing nozzle could be applied. Then, another dielectric spanning perhaps 30 degrees may be applied. Finally, a conductive outer shield, spanning perhaps 90 degrees and occupying the edges for electrically contacting the needle may be applied. This would create a smoothly encapsulated stripline structure spanning 90 degrees of the circumference, providing excellent shielding while saving on material and deposition time.

At the hub end portion, the bare needle surface, the hub contact or electrode, and outer shield, may form three circular contact pads that a small connector may clamp onto. This design minimizes connector cost on the disposable needle and puts the more costly part of the connection on a reusable clamp (not shown) that would connect to the needle and other contacts. This embodiment can be implemented using additive manufacturing technologies such as, for example, conformal micro dispensing systems or inkjet deposition techniques.

To keep the product cost down, the materials used should be low cost, and the manufacturing process should be highly automated with large volume to avoid labor and equipment cost. Given these goals, piezoelectrical polymers such as PVDF and P(VDF-TrFE) are candidate materials for sensor production. The ability of an applied voltage to produce motion in a PVDF sample is used to produce ultrasonic waves which can be detected using a PVDF based hydrophone. There are a wide variety of considerations in deciding whether to use a ceramic based piezoelectric or PVDF in a given medical application. At lower frequencies thicker PVDF membranes should be employed for resonance considerations. A PVDF sensor can be modeled as a voltage source in series with a capacitance and for thicker sensors with small surface area, this may result in a small capacitance. Hence, in general, it appears that PVDF has advantages for medical ultrasonic work carried out in the frequency range 25-100 MHz. PVDF is also limited in ability to transmit higher intensities of ultrasound compared to PZT.

PVDF has favorable behavior even at the lower frequencies, for example, for PVDF hydrophones for detecting ultrasonic waves. Compared to PZT, which may also be employed in some embodiments, PVDF has a much higher bandwidth and will thus not distort the transient behavior of the wave as much. The low output capacitance problem can in this case be handled by integrating a high input impedance field effect transistor (FET) based preamplifier in very close proximity to the sensor. The d33 constant, strain in thickness direction developed for an applied voltage, is about an order of magnitude higher for piezo-ceramics than for piezo-polymers. One disadvantage of piezo-ceramic is its high acoustic impedance, about 30 MRayls (1 MRayl=106 kg/m$^2$s) in contrast to about 1.5 MRayls for body tissue. This impedance mismatch can be compensated by quarter wavelength matching layers, but these can degrade the ultrasonic pulse due to adhesive layers and construction methods. The acoustic impedance of piezo film is about 4 MRayls, a much better match. Additionally, ceramics are fragile, and cannot be shaped to desired geometries. PVDF is a conformable and flexible low cost material with acoustic impedance close to tissue that unlike PZT will not need matching layers.

PVDF piezoelectric films are produced in a clean room environment, and start with a melt extrusion of PVDF resin pellets into sheet form. Next, there is a stretching step that reduces the sheet thickness by about a factor of 5. This stretching, well below the melting point of the polymer, causes chain packing of the molecules into parallel crystal planes, called the "beta phase". To obtain high levels of piezoelectric activity, the beta phase polymer is then exposed to very high electric fields to align the crystallites relative to a poling field. In the stretching step, the film can be stretched along only one dimension (uni-axial film) or in both dimensions (bi-axial film). Bi-axial films will have their piezoelectric sensitivity primarily only in the thickness direction, while the uni-axial film will be sensitive to strain in both the thickness direction and the non-stretched planar direction.

New copolymers of PVDF have been developed that allow for use at higher temperatures (e.g., as high as 135 degrees Celsius for some copolymers, versus 100 degrees Celsius for conventional PVDF). Although these temperatures are not encountered in clinical use, a higher temperature tolerance can be an advantage in simplifying the manufacturing and sterilization process. Copolymers of PVDF are polarizable without stretching and very thin films down to 200 Angstroms can be produced using spincast coating techniques, such thin layers are not feasible with standard PVDF. In addition, the copolymer has a slightly higher thickness mode piezoelectric constant, leading to about 10% higher sensitivity compared to PVDF.

There are some electronic strategies to lessen the effect of parasitic capacitance on performance. One such technique is called "driven shield". A key element in this method is to reduce parasitic current flow from the wire carrying the signal of interest by minimizing the electric field surrounding it. This employs a total of three conductors in the interconnect, a ground connection, a signal wire, and a shield surrounding the signal wire. The voltage on the signal wire is measured and the shield is driven with an exact replica of that voltage. Even though the signal wire has a parasitic capacitance to the shield there is no parasitic current flowing as there are no voltage changes over the parasitic capacitance. The ground wire is held at a steady voltage by the amplifier power supply and not driven by the sensor, thus its parasitic capacitance to other structures has no detrimental influence. Another technique includes using a capacitance canceling amplifier (CCA).

The present principles have been described in terms of a needle, and more particularly to a biopsy needle. However, the present principles may be applied to any instrument where a sensor (receiver), transmitter or transducer is needed. Such devices may include catheters, guidewires, endoscopes, implantable devices, etc. The present principles can provide a relatively low cost device with a built-in for sensor conformally applied to an exterior surface. To keep the product cost down, the materials used need to be low cost, and the manufacturing process should be highly automated with large volume to avoid labor and equipment cost. The devices in accordance with the present principles provide a low form factor that is conformally formed and placed on a medical device or instrument. In particularly useful embodiments, the present principles are employed for ultrasound guided needle interventions, e.g., RF ablation, liver biopsy, nerve blocks, vascular access, abscess drainage, etc.

Figure 3:
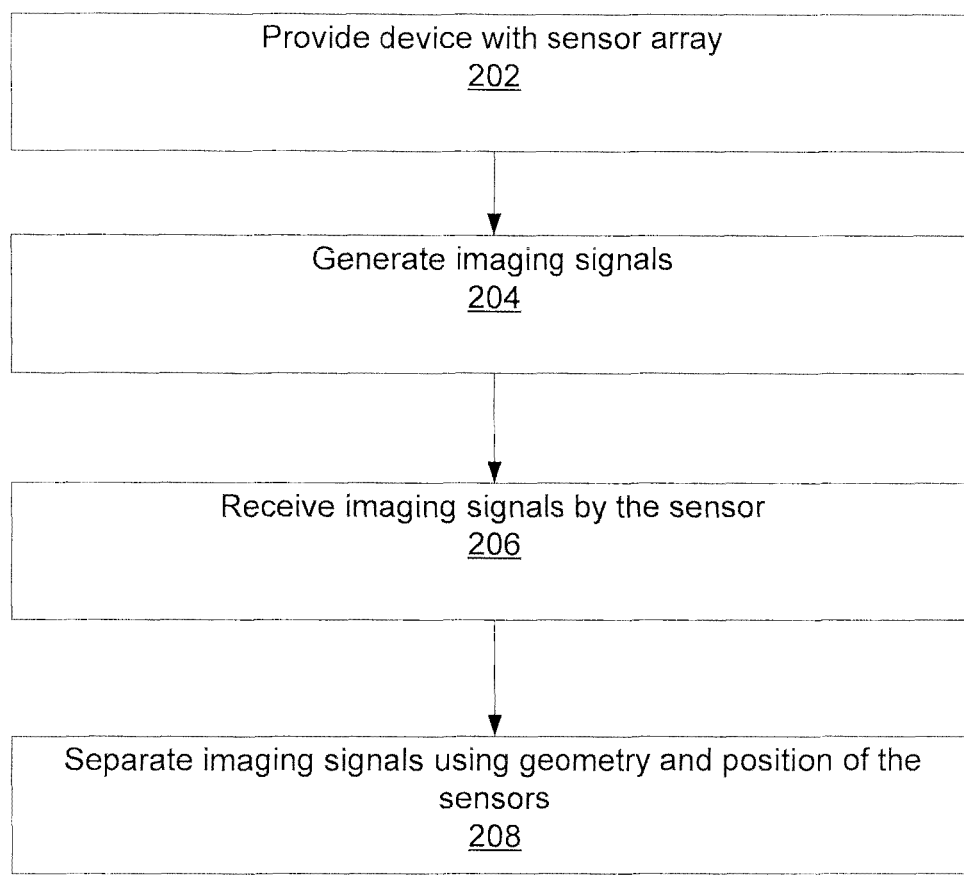
FIG. 3 is a flow diagram showing a method for separating signals received by a medical device having a plurality of sensors in accordance with illustrative embodiments.

Referring to FIG. 3, a method for deciphering received signals in a medical device is shown in accordance with the illustrative embodiments. In block 202, a medical device is provided having an elongated body, a plurality of sensors conformally formed on the elongated body at a plurality of longitudinal positions along the elongated body, an electrical trace connecting to the plurality of sensors, the plurality of sensors being connected in parallel to form an array of sensors along the elongated body. The number of sensors may include two or more or three or more. In block 204, signals are generated at a position by an imaging system. The imaging system preferably includes an ultrasound system although other imaging systems may benefit from the present principles. In block 206, the signals are received by the plurality of sensors. In block 208, the signals received by the plurality of sensors are separated by employing variable spacings between and geometric positions of the plurality of sensors to determine which sensor received which signals. The variable spacings between the sensors and geometric positions of the sensors provide different delays from which sensors are determined in the signals. In one embodiment, the elongated body includes a needle and an inserted distance of the needle is employed to determine which sensor received which signals.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for needle with multiple sensors (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device configured for use with an imaging system having a beam scanning probe at an imaging position, comprising:

an elongated body;

a plurality of sensors conformally disposed on the elongated body at a plurality of longitudinal positions along the elongated body, the plurality of sensors being configured to generate signals in accordance with detected energy for the imaging system, and being spaced apart from adjacent sensors by a respective one of a plurality of spaces, each of the plurality of spaces having a distance configured to cause a respective delay in signals measured at the respective one of the plurality of sensors; and a single electrical trace connected to each of the plurality of sensors and electronic circuitry, the plurality of sensors connected in parallel to provide an array of sensors along the elongated body, wherein the electronic circuitry is configured to determine which sensor received each measured signal by separating the measured signals based on the respective delay, and wherein the electronic circuitry is configured to track a relative position of the elongated body to the imaging position of the beam scanning probe based on the determination of which sensor received each measured signal.

2. The medical device as recited in claim 1, wherein the plurality of sensors include piezoelectric polymer sensors.

3. The medical device as recited in claim 1, wherein each of the plurality of sensors is conformally disposed around at least a portion of a circumference of the medical device.

4. The medical device as recited in claim 1, wherein the elongated body includes a needle.

5. The medical device as recited in claim 1, wherein the single electrical trace is connected to a hub contact, the hub contact providing an electrical contact that connects the single electrical trace to the electronic circuitry configured to process and measure the signals received at the plurality of sensors.

6. The medical device as recited in claim 1, wherein the single electrical trace includes one of conductive ink or a deposited layer.

7. The medical device as recited in claim 1, wherein the plurality of sensors comprises a tip sensor, a middle sensor and a hub side sensor, and distance between the tip sensor and the middle sensor is different than distance between the middle sensor and the hub side sensor.

8. The medical device as recited in claim 1, wherein distance between at least two of the plurality of sensors is not the same.

9. The medical device as recited in claim 1, further comprising a conductive shield disposed over the single electrical trace on a dielectric material.

10. The medical device as recited in claim 9, wherein the conductive shield forms a common electrode for the plurality of sensors.

11. The medical device as recited in claim 1, further comprising:
an electrical insulator disposed over the elongated body, the electrical insulator having a plurality of gaps along its length, wherein each of the plurality of sensors is located at a respective one of the plurality of gaps.

12. The medical device as recited in claim 11, further comprising:
another electrical insulator disposed over the single electrical trace and the electrical insulator; and
an insulator and metallization layer disposed over the elongated body, the insulator and metallization layer forming an inner shield for the medical device, whereby the plurality of sensors are disposed over of the insulator and metallization layer, and are insulated from the elongated body.

13. A medical device configured for use with an imaging system having a beam scanning probe at an imaging position, comprising:
an elongated body;
three or more sensors conformally disposed on the elongated body at a plurality of longitudinal positions along the elongated body, the three or more sensors being spaced apart from adjacent sensors by a respective one of a plurality of spaces, each of the plurality of spaces having a distance configured to cause a respective delay in signals measured at the respective one of the plurality of sensors, the three or more sensors being configured to generate signals in accordance with detected energy for the imaging system; and
an electrical trace connected to the three or more sensors and electronic circuitry, the three or more sensors being connected in parallel to form an array of sensors along the elongated body, wherein the electronic circuitry is configured to determine which sensor received each measured signal by separating the measured signals based on the respective delay, and
wherein the electronic circuitry is configured to track a relative position of the elongated body to the imaging position of the beam scanning probe based on the determination of which sensor received each measured signal.

14. The medical device as recited in claim 13, wherein the three or more sensors include piezoelectric polymer sensors.

15. The medical device as recited in claim 13, wherein each of the three or more sensors is conformally disposed about at least a portion of a circumference of the medical device.

16. The medical device as recited in claim 13, wherein the elongated body includes a needle.

17. The medical device as recited in claim 13, wherein the electrical trace is connected to a hub contact, the hub contact providing an electrical contact that connects the electronic circuitry configured to process and measure the signals received at the three or more sensors.

18. The medical device according to claim 13, wherein distance between at least two of the three or more sensors is not the same.

19. The medical device according to claim 13, wherein the three or more sensors further comprise a tip sensor, a middle sensor and a hub side sensor, and distance between the tip sensor and the middle sensor is different than distance between the middle sensor and the hub side sensor.

20. The medical device as recited in claim 13, further comprising a conductive shield disposed over the electrical trace on a dielectric material.

21. The medical device as recited in claim 20, wherein the conductive shield forms a common electrode for the three or more sensors.

22. The medical device as recited in claim 13, further comprising:
an electrical insulator disposed over the elongated body, the electrical insulator having a plurality of gaps along its length, wherein each of the three or more sensors is located at a respective one of the plurality of gaps.

23. The medical device as recited in claim 22, further comprising:
another electrical insulator disposed over the electrical trace and the electrical insulator; and
an insulator and metallization layer disposed on the elongated body, the insulator and metallization layer forming an inner shield for the medical device, whereby the three or more sensors are disposed over of the insulator and metallization layer, and are insulated from the elongated body.

* * * * *